United States Patent [19]

Nash

[11] Patent Number: 4,484,891
[45] Date of Patent: Nov. 27, 1984

[54] VIBRATORY ENDODONTIC DEVICE

[75] Inventor: John E. Nash, Downingtown, Pa.

[73] Assignee: Syntex (U.S.A.) Inc., Palo Alto, Calif.

[21] Appl. No.: 433,075

[22] Filed: Oct. 6, 1982

[51] Int. Cl.³ .............................................. A61C 1/16
[52] U.S. Cl. ..................................... 433/116; 433/75; 433/118; 433/128
[58] Field of Search ............... 433/116, 118, 119, 120, 433/122, 123, 126, 127, 128, 129, 102, 75, 76, 224

[56] References Cited

U.S. PATENT DOCUMENTS

| Re. 29,687 | 7/1978 | Sertich ................................ | 433/120 |
|---|---|---|---|
| 349,338 | 9/1886 | Buschemeyer ..................... | 433/122 |
| 1,046,560 | 12/1912 | Coulson ............................... | 433/122 |
| 1,821,079 | 9/1931 | Schultze .............................. | 433/122 |
| 2,690,617 | 10/1954 | Giern et al. ......................... | 433/147 |
| 3,037,282 | 6/1962 | Aktarian et al. .................... | 433/128 |
| 3,058,218 | 10/1962 | Kleesattel et al. ................. | 433/119 |
| 3,786,566 | 1/1974 | Jelicic et al. ........................ | 433/116 |
| 3,892,040 | 7/1975 | Marquis .............................. | 433/147 |
| 3,962,790 | 6/1976 | Riitano et al. ...................... | 433/81 |
| 4,262,252 | 5/1981 | Lustig ................................. | 433/116 |

FOREIGN PATENT DOCUMENTS

| 808873 | 7/1949 | Fed. Rep. of Germany ...... | 433/118 |
|---|---|---|---|
| 1084870 | 7/1960 | Fed. Rep. of Germany ........ | 433/75 |
| 3010636 | 10/1981 | Fed. Rep. of Germany ...... | 433/119 |

*Primary Examiner*—John J. Wilson
*Attorney, Agent, or Firm*—David A. Lowin; John A. Dhuey

[57] ABSTRACT

A vibratory endodontic device is described for mechanical preparation of dental radicular canals, i.e., root canals, prior to their obturation. The device includes a housing, a vibratory drive means supported within the housing to minimize the transfer of vibration to the housing, an endodontic file connected to the drive means for vibratory movement and stop means operatively connected to the housing and substantially isolated from the mechanical vibrations created by the vibratory drive means. Additionally, fluid transport means are provided for maintaining a continuous flow of irrigation fluid along the endodontic file. Various assemblies for retaining the endodontic files on the operative end of the vibrating device are also described.

14 Claims, 16 Drawing Figures

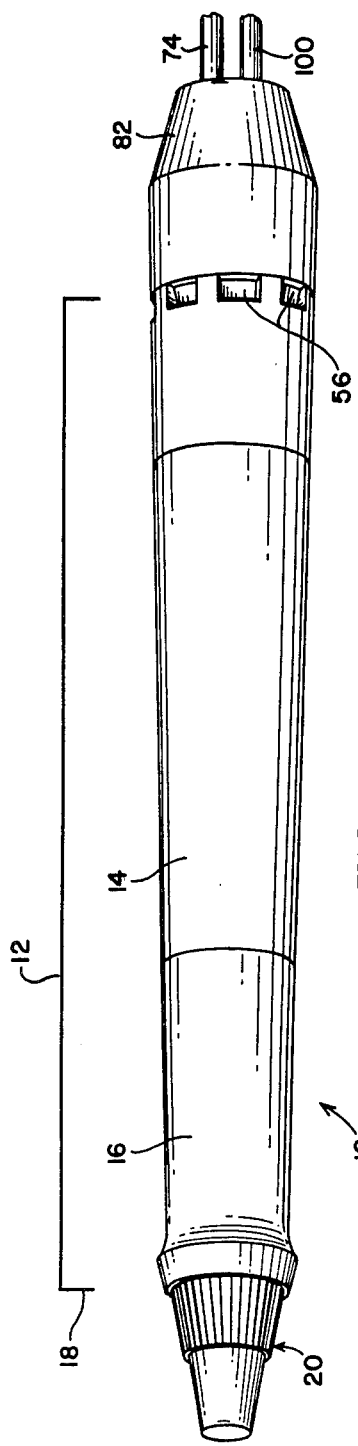
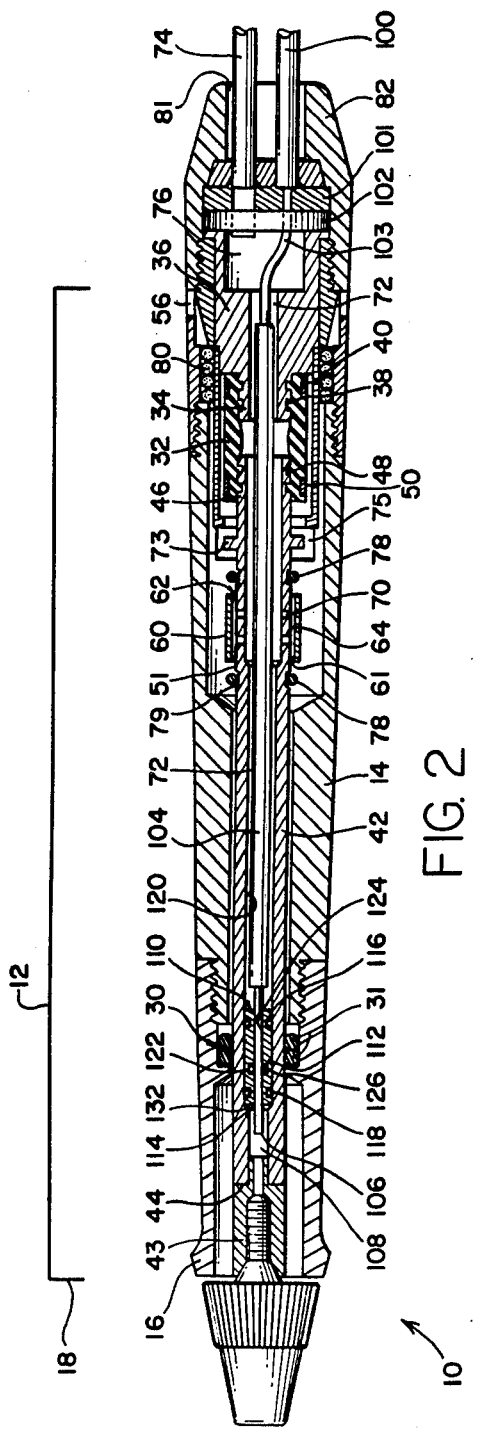

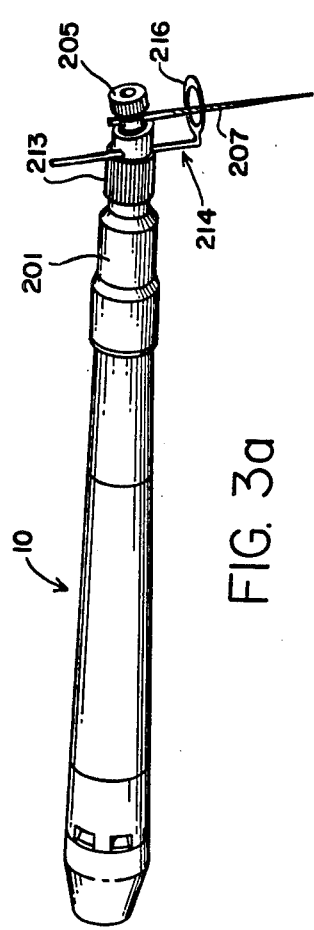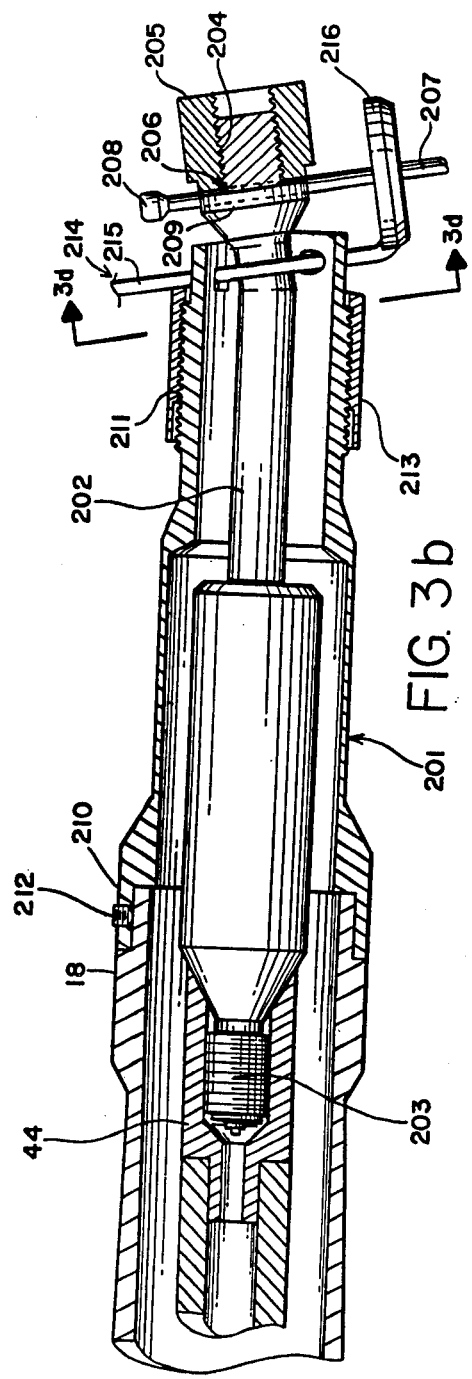

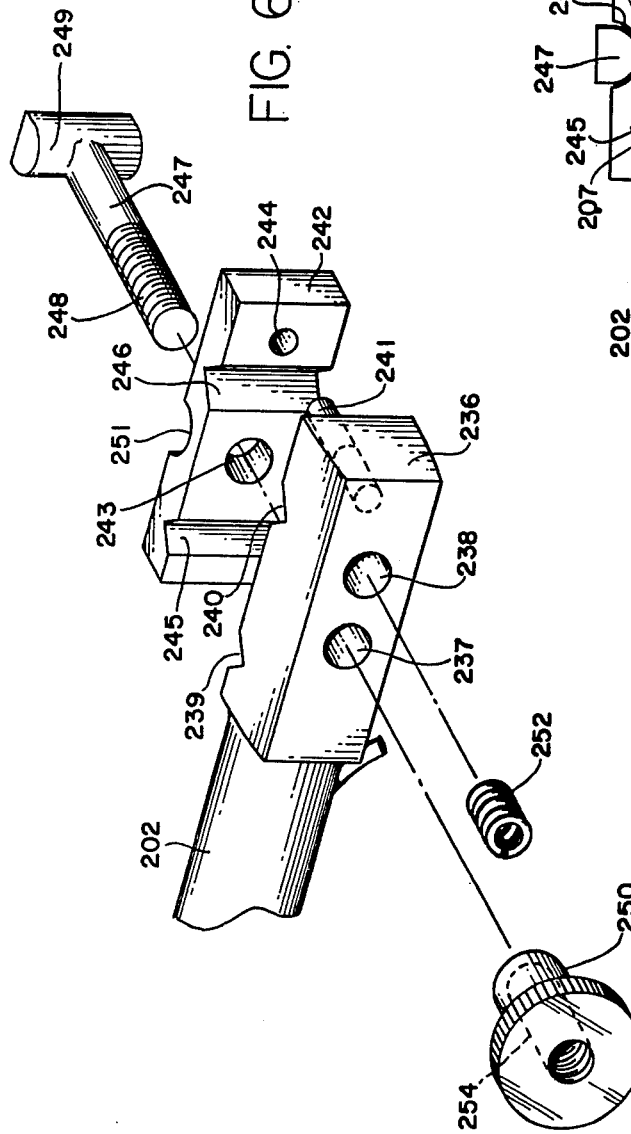

VIBRATORY ENDODONTIC DEVICE

BACKGROUND OF THE INVENTION

1. Field

This invention relates generally to mechanically driven endodontic instruments. In particular, it relates to a vibratory endodontic device having stop means to limit travel of the endodontic file during use that are substantially isolated from the mechanical vibrations created by the vibratory drive mechanism of the device and optionally, having fluid transport means for transporting irrigation fluid to the endodontic file.

2. State of the Art

Mechanically driven endodontic instruments have been describe previously, as for example in U.S. Pat. Nos. 3,598,745 and 3,962,790. Various stops have been described for limiting the depth of insertion of endodontic file during use. See for example, U.S. Pat. Nos. 3,961,422; 4,028,810; 4,165,562 and 4,182,040. Conventional methods of controlling the depth of insertion of mechanically driven endodontic files have not been satisfactory. When conventional stops are placed directly on the endodontic files which are driven by mechanical devices, the stops tend to fail rapidly themselves and also tend to increase the failure rate of files used therewith. Additionally, the added mass of the stop on the file tends to affect the vibratory action of the file and the control thereof.

Accordingly, there is a need for an improved stop mechanism for use with mechanically or electrically driven endodontic files.

SUMMARY OF THE INVENTION

As used herein, the term "mechanically driven" or "mechanical" includes vibratory devices those devices which are powered by means other than the dentist's or doctor's hand. Such mechanically driven vibratory devices are intended to include strictly mechanically driven devices such as gear driven handpieces which impart an oscillatory, to-and-fro motion to a work tool, fluid driven devices such as of the type more particularly described herein and electrically driven devices.

The present invention in one aspect is a vibratory endodontic device comprising a housing; vibratory drive means within the housing; means supporting the vibratory drive means within the housing, the supporting means substantially preventing transfer of vibration between the vibratory drive means and the housing; a work tool (such as an endodontic file) operatively connected to the vibratory drive means; and stop means operatively connected to the housing for limiting travel of the work tool between selected positions during use thereof, whereby the stop means is substantially isolated from vibration created by the vibratory drive means.

In another aspect, the invention is directed to an assembly for attaching a work tool (i.e., endodontic file) to a vibratory device, such assembly comprising an elongated mandrel having a first end for attachment to the vibratory device and a second end for supporting the work tool, and retaining means on the second end of the mandrel for retaining both a work tool thereon and a stop for selectively limiting travel of the file when in use.

BRIEF DESCRIPTION OF THE DRAWINGS

FIG. 1 is a perspective view of a representative vibratory device for powering a work tool assembly (not shown) to be attached thereto;

FIG. 2 is a longitudinal side elevational view, partly in section, of the vibratory device of FIG. 1;

FIG. 3A is a perspective view of a presently preferred embodiment of the vibratory endodontic device of the invention;

FIG. 3B is cross-sectional view of the work tool assembly of the device of FIG. 3A;

FIGS. 5A–5C and 6A–6B illustrate alternative means for supporting the work tool and stop means on the vibratory device.

DETAILED DESCRIPTION OF THE INVENTION

Figure 3D:
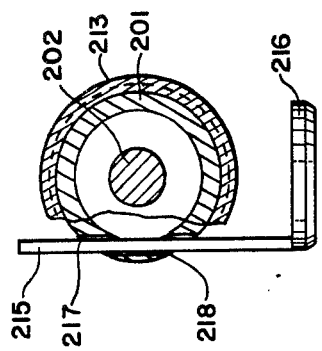
FIG. 3D is a cross-sectional view along line A—A of FIG. 3A illustrating the offset location of the stop means.
Figure 3C:
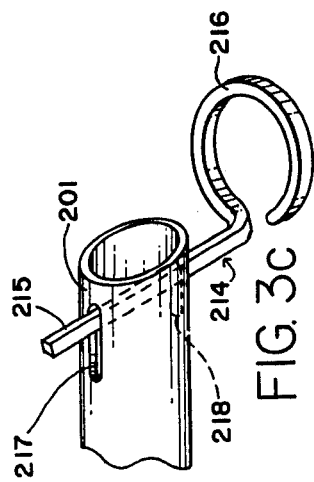
FIG. 3C is a detailed view of a stop means for use with the present invention.

With reference to the drawings, the vibratory device 10 comprises a housing having a handle 12 which includes a barrel 14 and a neck 16. Attached to the distal end 18 of the vibrator 10 is a tip holder 20. Tip holder 20 is adapted to receive the shank of a work tool such as an endodontic file, as will be described more fully hereinafter. As shown in detail in the cross-sectional view of FIG. 2, handle 12 provides an elongated casing within which is mounted support means comprising a first or front support 30 including a pair of O-rings 31. A second or rear resilient support is provided by a cylindrical tube 32 of resilient material which is sleevably engaged about a boss portion 34 secured to a rigid rear support 36. Boss portion 34 has a retaining grooves 38 circumferentially disposed thereon for retaining resilient rear support 32 by means of retaining ring 40. Disposed substantially coaxially with respect to elongated handle 12 is a vibratable, substantially rigid, hollow shaft 42. Tip holder 20 is threadedly connected to the distal end 44 of hollow shaft 42 and the proximal end of shaft 42 is formed with retaining grooves 48 for engaging resilient rear support 32 therein. A pin 73 is provided on shaft 42 for engaging a wall 75 of a slot in rear support 26 to oppose twisting forces applied to shaft 42 during engagement or disengagement of tip holder 20 with or from the distal end of shaft 42. Rear support 32 is retained within retaining grooves 48 on shaft 42 by means of a retaining ring 50.

As seen most clearly in FIG. 2, shaft 42 is formed with an intermediate section 51 having a diameter greater than the diameter of those portions of shaft 42 adjacent section 51. Outlet ports 70 are formed in the wall of shaft 42 in the intermediate section 51 and serve to provide fluid communication for fluid media means from the inside of tubular shaft 42 to the space adjacent side wall 64 of shaft 42. Centrally and axially disposed above intermediate portion 51 of shaft 42 is rotor means 60, which defines a gap 62 between its inner surface 61 and side wall 64 of shaft 42 into which fluid media is directed from outlet ports 70.

With reference to FIGS. 1 and 2, a fluid medium, such as compressed air, is supplied from a source (not shown) through a supply tube 74 which passes through an axially disposed opening 81 in end cap 82. The flow of compressed air passes into plenum 76 in through passageway 72 and shaft 42 to fluid media outlet ports 70. The flow of compressed air which exhausts through outlet ports 70 strikes the inner wall 61 of rotor 60 and urges rotor 60 to rotate about shaft 42. Each of the outlet ports 70 has an axis which is offset or spaced at a distance from the longitudinal axis of shaft 42. In that configuration no port axis intersects the longitudinal axis of shaft 42 and each of ports 70 directs a jet of air at a glancing angle with respect to the inner wall 61 of rotor 60 so as to impart rotational movement to rotor 60. The air passes through the end sections of gap 62 into the main barrel section and subsequently passes through muffler means 80 which are supported on rigid rear support 36 to exhaust through outlet ports 56 into the atmosphere.

Stop means 78 are disposed in indented sections or grooves 79 in outer surface 64 of shaft 42. Typically, stop means 78 comprise O-rings sleevably engaged about shaft 42. Stop means 78 prevent excessive travel of rotor 60 so that rotor 60 is at least partially disposed about outlet means 70 at all times, including the time prior to activation of the instrument with compressed air. Thus, when air is supplied to the instrument, the air flowing through outlet ports 70 will contact at least a portion of rotor 60 and initiate its rotational movement about shaft 42. In normal operation rotor 60 will not contact stop means 78. A more detailed description of the manner in which the spinning rotor 60 imparts vibrational movement to shaft 42 and other aspects of the vibrator may be found in the U.S. Pat. No. Re. 29,687 and U.S. Pat. No. 4,330,282, the disclosures of which are incorporated herein by reference.

The vibrator can include means for transporting water or other fluids (e.g. medicated irrigants) from an external source to a work tool at its operative end. A first fluid transport hose 100 located at the rearward or proximal end of vibrator 10 is mounted in a detachable coupling 101. First fluid hose 100 is connected to an external source of fluid (not shown), the forward end of the hose being connected to one end of a rigid tube 103 which passes through a passageway in support body 102. Tube 103 is disposed substantially coaxially with respect to hollow shaft 42. Fluid transport tube 103 extends through hollow shaft 42 toward the distal end of scaler 10 and terminates distally from fluid seal assembly 110. Tube 103 is covered with an elastomeric tube covering 104 to dampen vibration build-up within tube 103. The forward or distal end 106 of fluid tube 103 extends into plenum 108.

Fluid tube end 106 is supportably received within a fluid seal assembly 110 located at the forward or distal end of vibrator 10. Fluid seal assembly 110 comprises a cylindrical body 112 having a passageway 114 coaxially disposed with respect to the axis of body 112. Running circumferentially about the outer side wall of cylindrical body 112 are a pair of spaced annular grooves 116, one adjacent each end cylindrical body 112. Disposed within each of grooves 116 is an O-ring 118 fabricated of a resilient material. O-rings 118 serve to position cylindrical body 112 within the forward end of hollow shaft 42 by frictional engagement of O-rings 118 with portions of inner wall 120 of shaft 42. Within a midportion of cylindrical body 112 is a chamber formed by an annular groove 122 running circumferentially along a portion of inner wall 124 of body 112 between grooves 116. Contained within groove 122 is an O-ring 126 which is in frictional engagement with the walls of groove 122 and with a portion of fluid tube 106. O-ring 126 helps to properly position tube 104 centrally within hollow shaft 42. Positioning of the center of gravity of fluid seal assembly 110 slightly forwardly of first support 30, i.e., toward the distal end of scaler 10, imparts a force on cylindrical body 112 tending to move it in a forward axial direction toward the distal end of scaler 10, thereby ensuring continuous contact between cylindrical body 112 and shoulder 132 of shaft 42. A more detailed description of the manner in which sealing between the water assembly 110 and shaft 42 is effected is provided in U.S. Pat. No. 4,260,380, the disclosure of which is incorporated herein by reference.

In the presently preferred embodiment of the invention, the tip holder 20 of the vibratory device 10 is replaced by an extension 201 and a mandrel 202 for supporting the endodontic file 207. This embodiment is illustrated in FIGS. 3A–3D. As shown, extension 201 is formed at its end 210 with a surface suitable for engaging with a formed surface on the distal end 18 of the handle of the vibrator 10. The extension 201 is retained on the vibrator by means of a set screw 212. The other end of extension 201 is formed as a threaded end 211 adapted to engage a retaining ring 213 which is internally threaded. Extension 201 is formed with holes 217 and 218 to receive an adjustable stop 214. Stop 214 is formed with an upper leg 215 and a depending stop surface 216 from the lower end of the leg 215. Leg 215 is adapted to pass through holes 218 and 217 and can be moved upwardly and downwardly within those holes. When stop 214 has been moved to an appropriate selected position, retaining ring 213 is threaded forwardly toward end 211 such that it forces leg 215 forwardly until it is fixedly retained in holes 217 and 218. As can be seen most clearly in FIG. 3D, holes 217 and 218 are offset from the central longitudinal axis of the vibrator so as not to interfere with mandrel 202.

Mandrel 202 is formed with a threaded end 203 which is adapted to be received by threaded end 44 of hollow shaft 42. The other end of mandrel 202 extends from the forward end of extension 201 and is also formed with a threaded end 204. A vertical bore 206 is formed in mandrel 202 and is adapted to receive an endodontic file 207. Typically, file 207 is formed with an enlarged head 208 to prevent it from slipping downwardly through bore 206. A threaded nut 205 is provided on the threaded end 204 of mandrel 202 to firmly secure file 207 within bore 206. A collar 209 is optionally provided between file 207 and the end of extension 201 in order to lessen the possibility of shearing file 207 when nut 205 is tightened.

When vibrator 10 is energized, vibration is transmitted through hollow shaft 42 to mandrel 202 which further transfers the vibrational motion to file 207. The end of file 207 is typically moved in an eliptical or circular pattern by the vibratory motion of mandrel 202, which motion has been found to be very efficient to enlarge root canals and the like in teeth. However, as can be seen from the structure previously described, the stop member 214 is isolated from the vibrational transfer from hollow shaft 42 since it is suspended from housing 12, and not mandrel 202 which is directly connected to the vibrating member. Since hollow shaft 42 is resiliently supported within housing 12 by supports 30 and 32, minimal vibrational transfer occurs between hollow shaft 42 and housing 12. Stop member 214 then is effectively isolated from the vibrational transfer and accurate depth placement of the end of file 207 is possible. Furthermore, because minimal vibrations are transferred to stop member 214, the failure life of stop member 214 is accordingly extended.

Stop member 214 is advantageously formed from a square wire or a rectangular wire such that it can be automatically oriented with respect to the file 207 in the proper position by placement in a rectangular or square-shaped hole 217. It then is only necessary that the stop member 214 be moved vertically up or down to position it with respect to the end of file 207 for proper placement. Stop surface 216 is conveniently placed such that it circumscribes at least a portion of file 207 but does not touch the file during any of the vibratory motion imparted thereto. In that configuration, stop surface 216 is positioned to contact the tooth surface during use without regard to the particular orientation of the vibratory device 10 when the file 207 is located within the tooth during use.

Figure 4:
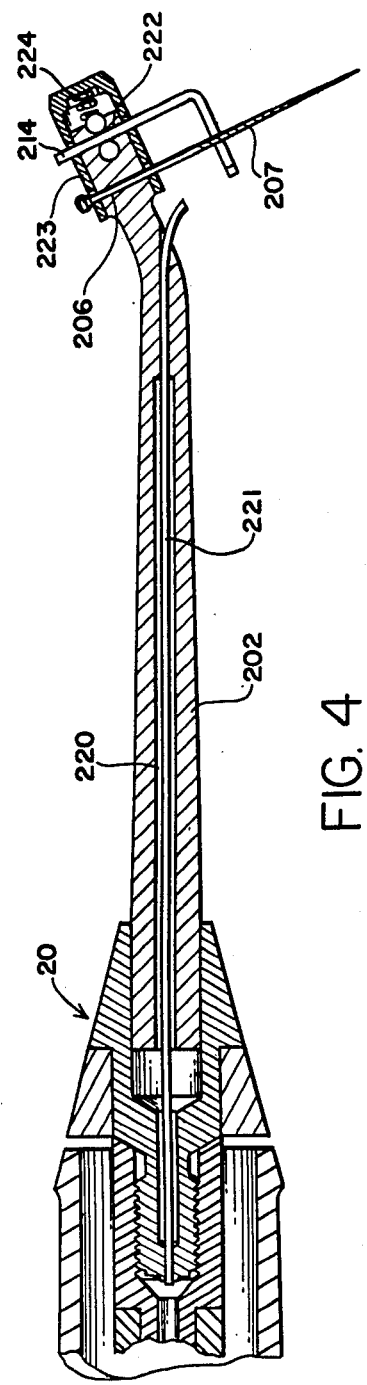
FIG. 4 is a side view, partially in section, of a work tool assembly incorporating fluid transport means.

In many instances it is desirable to provide a fluid, often containing a medicament, to the working end of file 207. Such can be accomplished by utilizing the vibrator described in FIG. 2 and the work tool assemby illustrated in FIG. 4. As shown in FIG. 4, the mandrel 202 is formed with a longitudinal bore 220 into which is inserted a tube 221. The distal end of 221 conveniently extends a short distance out from the distal end of mandrel 202 and fluid flow is directed directly on to file 207. The proximal end of tube 221 is in fluid communication with plenum 108 to receive and transport fluid from the vibratory device. The head portion of mandrel 202 is formed with vertical bores 206 and 222 which are adapted to receive file 207 and stop member 214, respectively. An end cap 223 having holes to accommodate the ends of file 207 and stop 214 is placed about the head of mandrel 202 and can be conveniently spring loaded with spring 224 to retain file 207 and stop member 214 in selected positions.

It will be apparent that a longitudinal bore such as bore 220 and a conduit such as tube 221 can be suitably placed within mandrel 202 which is illustrated in FIGS. 3A-3D with respect to the presently preferred embodiment. Such an irrigation feature is considered to be within the presently preferred embodiments.

Figure 5A:
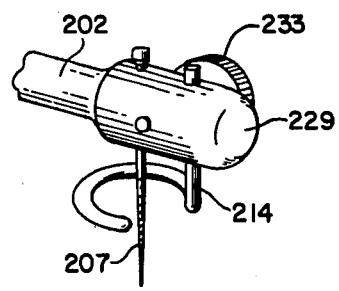
Figure 5B:
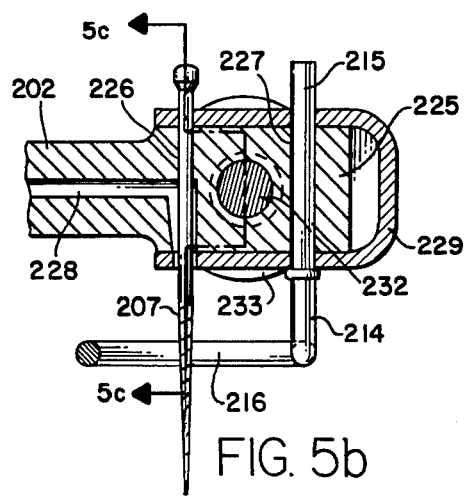
Figure 5C:
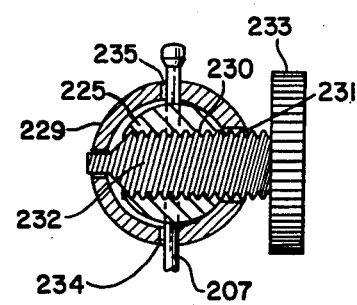

Various alternative embodiments for attaching the file 207 and stop member 214 to the mandrel 202 are illustrated in FIGS. 5, 6 and 7. However, those illustrated embodiments are presently considered to be less preferable then that illustrated in FIGS. 3A-3D. As shown in FIGS. 5A-5C, the mandrel 202 can be formed with a substantially cylindrical mandrel head 225 having a vertical bore 226 and a vertical bore 227 adapted to receive file 207 and stop member 214, respectively. Mandrel 202 can be provided with a longitudinal bore 228 which intersects bore 226 and provides a flow channel for transporting fluid to the end of file 207. File 207 and stop member 214 are fixedly retained in head 225 by means of a retaining tube 229 which is formed with top and bottom holes, designated as 235 and 234, respectively, to receive the upper ends of file 207 and stop member 214. The inner diameter of retaining tube 229 is made somewhat larger than the outer diameter of head 225 of mandrel 202. Mandrel 202 is provided with a transverse bore 230 which is internally threaded and adapted to receive a screw 232 which enters retaining tube 229 through a horizontal hole 231 formed in one side thereof. Conveniently a thumb wheel 233 is connected to screw 232 to assist the operator in its inward and outward movement. As can be seen most clearly in FIG. 5C, tightening of screw 232 moves retaining tube 229 to a position which forces file 207 and stop member 214 against the walls of their respective receiving bores in head 225 of mandrel 202. That force effectively maintains file 207 and stop member 214 in fixed positions during use.

In still another embodiment, as can be seen in FIGS. 6A and 6B, mandrel 202 is formed with a substantially rectangular head 236 having transverse bores 237 and 238 and vertical grooves 239 and 240. Vertical grooves 239 and 240 are adapted to receive file 207 and stop member 214, respectively, as can be seen most clearly in FIG. 6B. A locating pin 241 is conveniently fixed to head 236. A retaining plate 242 is provided opposite the grooved face of head 236, and retaining plate 242 is formed with a bore 243 and a hole 244. Bore 243 is adapted to receive a bolt 247 and is aligned with bore 237 in head 236. Bore 244 is adapted to receive locating pin 241 and the interaction of pin 241 with retaining plate 242 serves to prevent twisting of retaining plate 242 when the head 236 and retaining plate 242 are fastened together. Vertical grooves 245 and 246 are provided in the mating face of retaining plate 242 and are adapted to receive file 207 and stop member 214, respectively, as can again be seen most clearly in FIG. 6B. A substantially cylindrical groove extending vertically along the other face of retaining plate 242 is provided and groove 251 is dimensioned to mate with curved surface 249 formed on bolt 247. Retaining plate 242 and head 236 are secured by the engagement of bolt 247 on its threaded end 248 and a threaded nut 250. Bolt 247 extends through bores 243 and 237 and is received in threaded bore 254 in nut 250. A spring 252 is provided in bore 238 to load stop member 214 and minimize the vibration transmitted to stop member 214 during use of the instrument. A washer 253, as seen most clearly in FIG. 6B, can be interposed between nut 250 and the end of spring 252 to effectively retain spring 252 within bore 238.

Figure 7A:
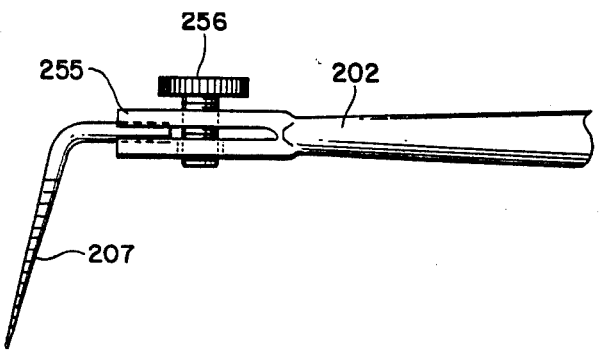
FIGS. 7A–7D illustrate alternative means for supporting a work tool on the vibratory device.
Figure 7B:
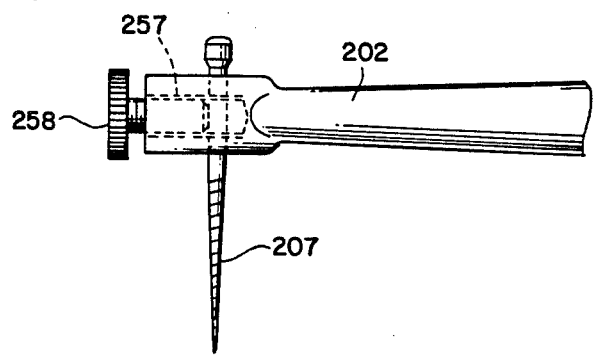
Figure 7C:
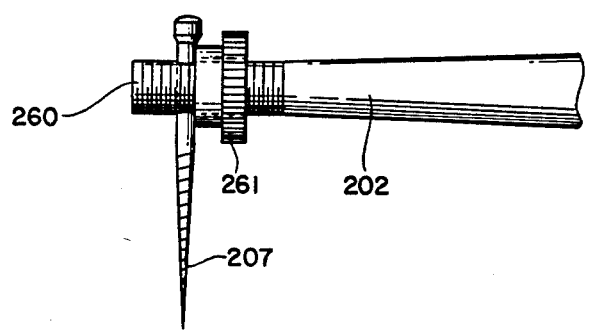
Figure 7D:
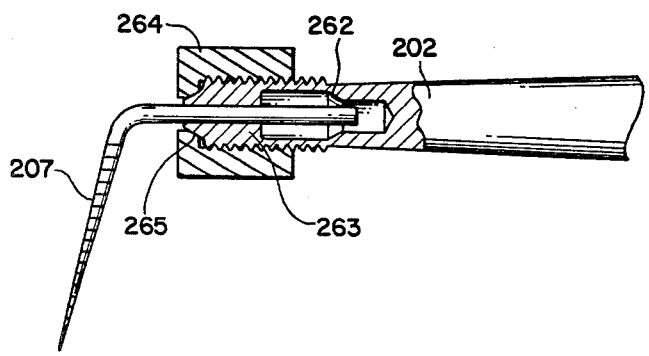

Various alternative configurations for retaining file 207 on the end of mandrel 202 are illustrated in FIGS. 7A-7D. As shown in FIG. 7A, mandrel 202 is provided with a split end 255 having a threaded bore and a screw 256 inserted therein. File 207 is inserted within the legs formed in split end 255 and can be retained therein by the pressure of screw 256. In FIG. 7B, mandrel 202 is provided with an internally threaded bore 257 in which is inserted a threaded screw 258 which bears against file 207 to retain it thereon. In FIG. 7C, the mandrel 202 is formed with a threaded end 260 having a bore there through to receive file 207. A captured, threaded nut 261 is positioned between file 207 and the vibratory portion of the device and can be tightened to press file 207 toward the forward end of end 260 to retain it thereon. In FIG. 7D, mandrel 202 is provided with a tapered bore 262 into which is inserted a collet 263 having split, tapered ends. A nut 264 having an internal tapered surface 265 is threadely received on the threaded end of mandrel 202. File 207 is received in collet 263 and when nut 264 is tightened, the tapered ends of collet 263 interact with the corresponding tapered surfaces of nut 264 and bore 262 to firmly grip file 207 and hold it in place.

While this invention has been described with reference to specific embodiments thereof, it should be understood by those skilled in this art that various changes may be made and an equivalents may be substituted without departing from the true spirit and scope of the invention. In addition, various novel elements, as described herein can be used individually or collectively, as desired. All such modifications are intended to be within the scope of the claims appended hereto.

What is claimed is:

1. A vibratory device comprising:
   a housing;
   vibratory drive means within said housing;
   means supporting said vibratory drive means within said housing, said support means substantially preventing the transfer of vibration between said vibratory drive means and said housing;
   a work tool operatively connected to said vibratory drive means;
   an adjustable stop means operatively connected to said housing for limiting travel of said work tool between selected positions during use of said vibratory device; and
   means for substantially isolating said stop means from vibration created by said vibratory drive means.

2. The vibratory device of claim 1 wherein said vibratory drive means includes a vibratable shaft within said housing and an elongated mandrel for supporting said work tool externally of said housing.

3. The vibrating device of claim 2 wherein said housing is substantially symmetrical about a central longitudinal axis and said stop means is attached to said housing at a position offset from the central axis.

4. The vibratory device of claim 3 wherein said stop means includes a support leg and a stop arm extending from said support leg, said support leg being adapted for connection to said housing and said stop arm being positionable adjacent said work tool said work tool extending beyond said stop arm by a distance selected to correspond to a desired limit of travel for said work tool with regard to an object to be worked on.

5. The vibratory device of claim 4 wherein said housing includes an opening for receiving said support leg and means for retaining said support leg within said opening.

6. The vibratory device of claim 5 wherein said retaining means includes a threaded portion on the end of the housing adjacent the opening and a threaded ring cooperatively engaging said threaded portion to be urged against said adjustable stop means for selecting and maintaining its position.

7. The vibratory device of claim 5 wherein at least a portion of said stop arm circumscribes a portion of said work tool.

8. The vibratory device of claim 5 wherein mating portions of said opening and said support leg are non-circular.

9. The vibratory device of claim 1 including fluid transport means adapted to transport fluid to the work tool.

10. The vibratory device of claim 9 wherein said vibratory drive means includes an elongated mandrel for supporting said work tool externally of said housing and said fluid transport means includes a conduit extending substantially the length of said mandrel and terminating adjacent said work tool, whereby fluid is transported from the inside of said housing to said work tool.

11. The vibratory device of claim 10 wherein said conduit is formed by a tube positioned within a bore formed in said mandrel.

12. An assembly for attaching an endodontic file to a vibratory device, said assembly comprising:
    an elongated mandrel having a first end adapted for attachment to the vibratory device and a second end for supporting a vibratory endodontic file;
    retaining means on said second ends of said mandrel for retaining a vibratory endodonite file;
    a stop for selectively limiting travel of the file when in use; and
    vibration isolated support means for retaining said stop and for substantially isolating said stop from vibration created by said vibratory device.

13. The assembly of claim 12 wherein said vibration-isolated support means comprises a tubular extension adapted to engage with said vibratory device and surrounding said elongated mandrel without contacting said elongated mandrel.

14. The assembly of claim 13 wherein said vibration-isolated support means concentrically surrounds said elongated mandrel and said stop is retained by said support means at an off-centered position to avoid contact with said elongated mandrel and said vibratory endodontic file.

* * * * *